(12) United States Patent
Woo et al.

(10) Patent No.: US 11,395,628 B2
(45) Date of Patent: Jul. 26, 2022

(54) METHOD OF PROVIDING SERVICE BASED ON BIOMETRIC INFORMATION AND WEARABLE ELECTRONIC DEVICE

(71) Applicant: SAMSUNG ELECTRONICS CO., LTD., Suwon-si (KR)

(72) Inventors: Jong Hyuk Woo, Yongin-si (KR); Byung Ki Moon, Seoul (KR); Sang Shik Park, Suwon-si (KR); Yong In Park, Seoul (KR); Seoung Jae Yoo, Seongnam-si (KR); Han Shin Shin, Yongin-si (KR); Kwan Hee Lee, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 459 days.

(21) Appl. No.: 15/837,338

(22) Filed: Dec. 11, 2017

(65) Prior Publication Data
US 2018/0228432 A1  Aug. 16, 2018

(30) Foreign Application Priority Data

Feb. 16, 2017 (KR) .................. 10-2017-0021002
Jun. 20, 2017 (KR) .................. 10-2017-0077894

(51) Int. Cl.
*A61B 5/00* (2006.01)
*A61B 5/0537* (2021.01)
(Continued)

(52) U.S. Cl.
CPC .......... *A61B 5/4872* (2013.01); *A61B 5/0537* (2013.01); *A61B 5/681* (2013.01);
(Continued)

(58) Field of Classification Search
CPC ... A61B 5/0537; A61B 5/1118; A61B 5/4872; A61B 5/681; A61B 5/742; A61B 5/7275;
(Continued)

(56) References Cited

U.S. PATENT DOCUMENTS 7,711,961 B2    5/2010  Fujinuma et al.
8,585,615 B2 *  11/2013  Kasahara ............. A61B 5/0537
                                                      600/547
(Continued)

FOREIGN PATENT DOCUMENTS

JP    2013-208374    10/2013
KR    10-0669169    1/2007
(Continued)

OTHER PUBLICATIONS

U.S. Office Action issued in corresponding U.S. Appl. No. 15/801,664 dated Jan. 22, 2020.
(Continued)

*Primary Examiner* — May A Abouelela
(74) *Attorney, Agent, or Firm* — F. Chau & Associates, LLC

(57) ABSTRACT

A method and apparatus provides a service based on biometric information. A bioelectrical impedance of a user is measured at a first time point to obtain a first value representing biometric information of the user. At least one processor predicts the biometric information of the user at a third time point subsequent to the first time point to obtain a third value, based on the first value representing biometric information of the user at the first time point and a second value representing the biometric information at a second time point prior to the first time point. The processor calculates a difference between a fourth value representing a target related to the biometric information of the user, input by the user in advance, and the third value. Information (Continued)

regarding a health management service is output based on the difference between the fourth value and the third value.

10 Claims, 16 Drawing Sheets

(51) Int. Cl.
| | |
|---|---|
| *G16H 20/30* | (2018.01) |
| *G06F 3/048* | (2013.01) |
| *G16H 20/60* | (2018.01) |
| *G16H 40/67* | (2018.01) |
| *G16H 50/30* | (2018.01) |
| *G04G 21/00* | (2010.01) |
| *G06T 11/20* | (2006.01) |

(52) U.S. Cl.
CPC ............. *G04G 21/00* (2013.01); *G06F 3/048* (2013.01); *G16H 20/30* (2018.01); *G16H 20/60* (2018.01); *G16H 40/67* (2018.01); *G16H 50/30* (2018.01); *A61B 5/7275* (2013.01); *A61B 5/742* (2013.01); *G06T 11/206* (2013.01)

(58) Field of Classification Search
CPC ..... A61B 5/053; A61B 5/6802; A61B 5/7271; G16H 40/67; G16H 50/30; G16H 20/30; G16H 20/60; G04G 21/00; G06F 3/048; G06T 11/206
USPC ................................. 600/300, 301, 547, 483
See application file for complete search history.

(56) References Cited

U.S. PATENT DOCUMENTS

| | | | | |
|---|---|---|---|---|
| 9,474,934 | B1* | 10/2016 | Krueger | G09B 19/003 |
| 9,554,274 | B1 | 1/2017 | Castinado et al. | |
| 10,007,709 | B2* | 6/2018 | Muto | G16H 20/60 |
| 2002/0123695 | A1* | 9/2002 | Kawanishi | A61B 5/0537 |
| | | | | 600/547 |
| 2002/0151815 | A1* | 10/2002 | Kawanishi | A61B 5/0537 |
| | | | | 600/547 |
| 2002/0183624 | A1 | 12/2002 | Rowe et al. | |
| 2003/0023186 | A1* | 1/2003 | Ueda | A61B 5/0537 |
| | | | | 600/547 |
| 2004/0059242 | A1* | 3/2004 | Masuo | A61B 5/0537 |
| | | | | 600/547 |
| 2004/0243020 | A1* | 12/2004 | Ueda | A61B 5/0537 |
| | | | | 600/547 |
| 2005/0209528 | A1* | 9/2005 | Sato | A61B 5/0537 |
| | | | | 600/547 |
| 2006/0235327 | A1* | 10/2006 | Masuo | A61B 5/0537 |
| | | | | 600/547 |
| 2006/0282005 | A1* | 12/2006 | Kasahara | A61B 5/0537 |
| | | | | 600/547 |
| 2007/0038140 | A1* | 2/2007 | Masuo | A61B 5/0537 |
| | | | | 600/547 |
| 2007/0043302 | A1* | 2/2007 | Masuo | A61B 5/0537 |
| | | | | 600/547 |
| 2008/0177569 | A1 | 7/2008 | Chen et al. | |
| 2009/0024053 | A1* | 1/2009 | Kasahara | A61B 5/0537 |
| | | | | 600/547 |
| 2009/0106563 | A1 | 4/2009 | Cherpantier | |
| 2009/0204018 | A1* | 8/2009 | Tseng | A61B 5/0537 |
| | | | | 600/547 |
| 2010/0100146 | A1* | 4/2010 | Blomqvist | A61B 5/0537 |
| | | | | 607/17 |
| 2011/0106553 | A1* | 5/2011 | Sato | A61B 5/4869 |
| | | | | 705/2 |
| 2011/0165996 | A1 | 7/2011 | Paulus et al. | |
| 2011/0245711 | A1* | 10/2011 | Katra | A61B 5/7225 |
| | | | | 600/547 |
| 2012/0004570 | A1* | 1/2012 | Shimizu | A61B 5/4872 |
| | | | | 600/547 |
| 2012/0253206 | A1* | 10/2012 | Fukuda | A61B 5/0452 |
| | | | | 600/483 |
| 2013/0197389 | A1* | 8/2013 | Levin | A61B 5/0537 |
| | | | | 600/547 |
| 2014/0031713 | A1* | 1/2014 | Gaw | A61B 5/0537 |
| | | | | 600/547 |
| 2014/0142459 | A1* | 5/2014 | Jayalth | A61B 5/0022 |
| | | | | 600/547 |
| 2014/0212850 | A1* | 7/2014 | Shimizu | A61B 5/0537 |
| | | | | 434/127 |
| 2014/0243699 | A1* | 8/2014 | Wabel | A61B 5/4875 |
| | | | | 600/547 |
| 2014/0245784 | A1* | 9/2014 | Proud | G06Q 40/04 |
| | | | | 63/1.11 |
| 2014/0288435 | A1* | 9/2014 | Richards | A61B 5/14539 |
| | | | | 600/479 |
| 2014/0343443 | A1* | 11/2014 | Yuen | G06F 19/3418 |
| | | | | 600/509 |
| 2015/0093725 | A1* | 4/2015 | Baarman | G09B 5/00 |
| | | | | 434/127 |
| 2015/0220109 | A1 | 8/2015 | Von Badinski et al. | |
| 2015/0310444 | A1 | 10/2015 | Chen et al. | |
| 2015/0347689 | A1 | 12/2015 | Neagle | |
| 2015/0373019 | A1 | 12/2015 | El Saddik et al. | |
| 2015/0379238 | A1* | 12/2015 | Connor | G16H 20/60 |
| | | | | 702/19 |
| 2016/0234206 | A1 | 8/2016 | Tunnell et al. | |
| 2016/0249857 | A1* | 9/2016 | Choi | A61B 5/0537 |
| | | | | 600/547 |
| 2016/0302677 | A1* | 10/2016 | He | A61B 5/02125 |
| 2016/0359864 | A1 | 12/2016 | Dhaliwal et al. | |
| 2016/0378100 | A1 | 12/2016 | Dow et al. | |
| 2017/0143268 | A1* | 5/2017 | Kovacs | A61B 5/1036 |
| 2017/0148240 | A1* | 5/2017 | Kovacs | H04L 63/0876 |
| 2017/0149773 | A1* | 5/2017 | Kovacs | H04L 63/0428 |
| 2018/0199824 | A1* | 7/2018 | Centen | A61B 5/7203 |
| 2019/0357776 | A1* | 11/2019 | Carreon | A61B 5/0022 |

FOREIGN PATENT DOCUMENTS

| | | |
|---|---|---|
| KR | 10-0974815 | 8/2010 |
| KR | 10-2015-0136808 | 12/2015 |
| KR | 10-1584090 | 1/2016 |
| KR | 10-2016-0016263 | 2/2016 |
| KR | 10-1624525 | 5/2016 |
| KR | 10-2016-0063341 | 6/2016 |
| KR | 10-1701114 | 2/2017 |

OTHER PUBLICATIONS

Office Action dated Jun. 27, 2019 in related U.S. Appl. No. 15/801,664.

U.S. Office Action issued in corresponding U.S. Appl. No. 15/801,664 dated Nov. 25, 2020.

Korean Office Action issued in corresponding Korean application No. 10-2017-0077894 dated Sep. 3, 2021.

* cited by examiner

METHOD OF PROVIDING SERVICE BASED ON BIOMETRIC INFORMATION AND WEARABLE ELECTRONIC DEVICE

CROSS-REFERENCE TO RELATED APPLICATIONS

This application claims benefit of priority to Korean Patent Application No. 10-2017-0021002, filed on Feb. 16, 2017, and Korean Patent Application No. 10-2017-0077894, filed on Jun. 20, 2017 in the Korean Intellectual Property Office, the disclosures of which are incorporated by reference herein.

1. Technical Field

The present inventive concept relates to a method of providing a service based on biometric information and to a wearable electronic device.

2. Discussion of the Related Art

As biosensors, which obtain biometric information of users, have become more commonly used, various applications using biometric information have been developed. In the related art, biometric information obtained by electronic devices including biosensors was merely provided to users. Recently, however, a large amount of research to provide users with more valuable applications using biometric information has been undertaken.

SUMMARY

The present, inventive concept may provide a useful service to a user by using biometric information obtained by an electronic device including a biosensor. In addition, the present inventive concept may include a wearable electronic device providing a service based on biometric information.

According the present inventive concept, a method of providing a service may include measuring by the biosensor a bioelectrical impedance of a user at a first time point to obtain a first value representing biometric information of the user; predicting, by a processor of the electronic device, the biometric information of the user at a third time point subsequent to the first time point, to obtain a third value, by utilizing the first value representing biometric information of the user at the first time point and a second value representing the biometric information of the user at a second time point prior to the first time point; calculating, by the processor, a difference between a fourth value representing a target related to the biometric information of the user, input by the user in advance, and the third value; and outputting, by the electronic device, information to the user regarding a health management service based on the difference between the fourth value and the third value.

According to an embodiment of the present inventive concept, a method of providing a service by an electronic device including at least one biosensor may include receiving body information from a user; measuring, by the at least one biosensor, bioelectrical impedance of the user at a first time point; obtaining biometric information of the user from the bioelectrical impedance and the body information; and displaying at least two of a plurality of parameters included in the body information and the biometric information, in a single graph.

According to an embodiment of the present inventive concept, a method of providing a service may include obtaining a fat mass and a body mass index (BMI) of a user; obtaining body type information of the user by inputting the fat mass and the BMI of the user to a database providing a classification standard of a body type based on the fat mass and the BMI; and providing the body type information to the user.

According to an embodiment of the present inventive concept, a wearable electronic device may include a body part including a circuit board having a biosensor to obtain biometric information of a user, a display outputting the biometric information of the user, a first surface on which the display is disposed, and a second surface opposing the first surface; a first electrode part including a pair of electrodes disposed to be adjacent, to each other on the first surface; a second electrode part, including a pair of electrodes disposed to be adjacent to each other on the second surface; and a fixing part to fix the body part to a body of the user. At least, one of the first electrode part and the second electrode part, is connected to a contact part of the circuit board by an operation in which the user presses the second surface.

In an embodiment of the inventive concept, the outputting of the information to the user regarding the health management service is displayed by the electronic device.

In an embodiment of the inventive concept, the outputting of the information to the user regarding the health management service is wirelessly transmitted to a mobile device of the user.

In an embodiment of the inventive concept, the outputting of the information to the user regarding the health management service may be initiated by sending a link to a mobile device of the user.

In an embodiment of the inventive concept, in response to the user selecting a link to access information from the health management service, performing an authentication procedure to displaying information regarding the health management service.

BRIEF DESCRIPTION OF THE DRAWINGS

The above features and other teachings of the present inventive concept will be more clearly understood from the following detailed description, when taken in conjunction with the accompanying drawings, in which.

DETAILED DESCRIPTION

Hereinafter, example embodiments of the present inventive concept will be described with reference to the attached drawings.

Figure 1:
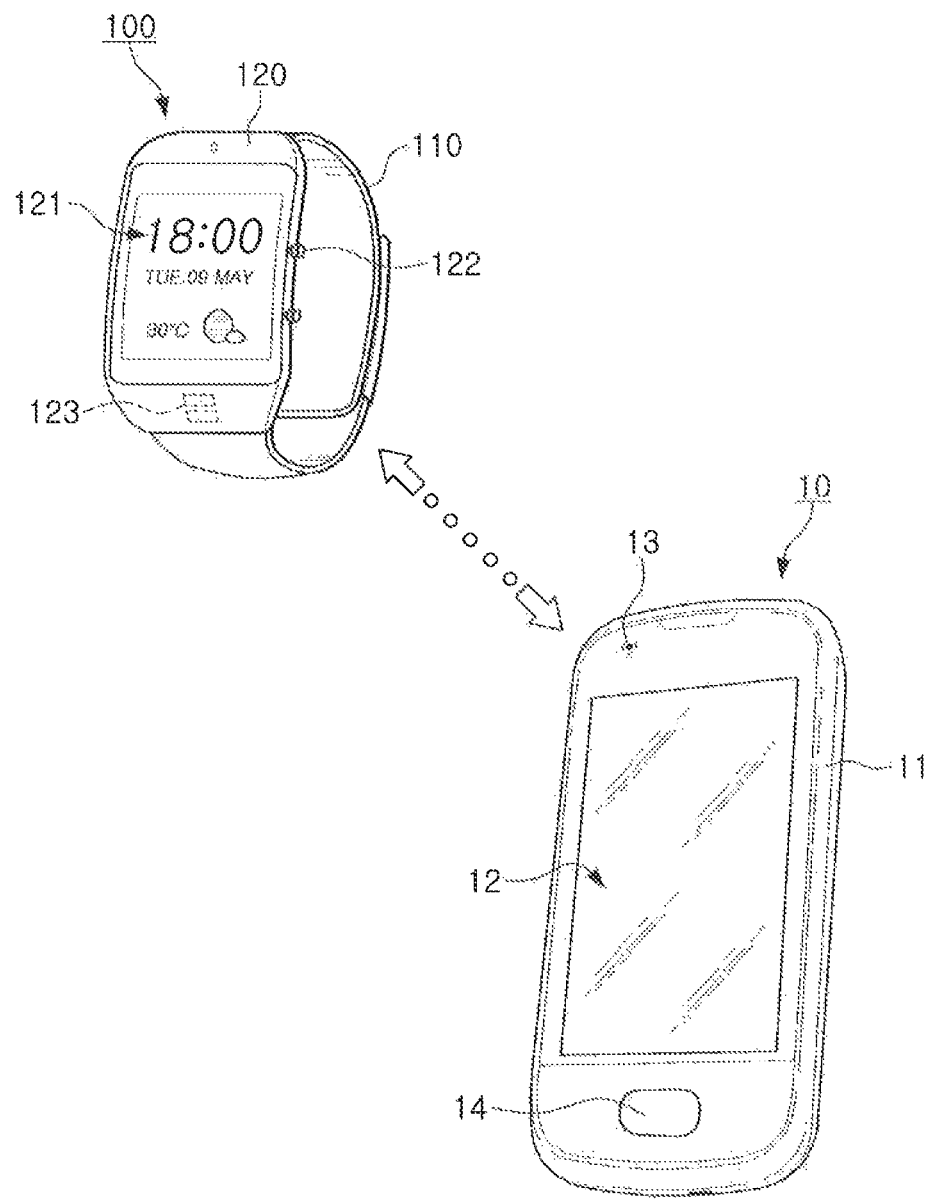
FIG. 1 is a view of a wearable electronic device communicating with a mobile device according to an example embodiment of the inventive concept.
Figure 2:
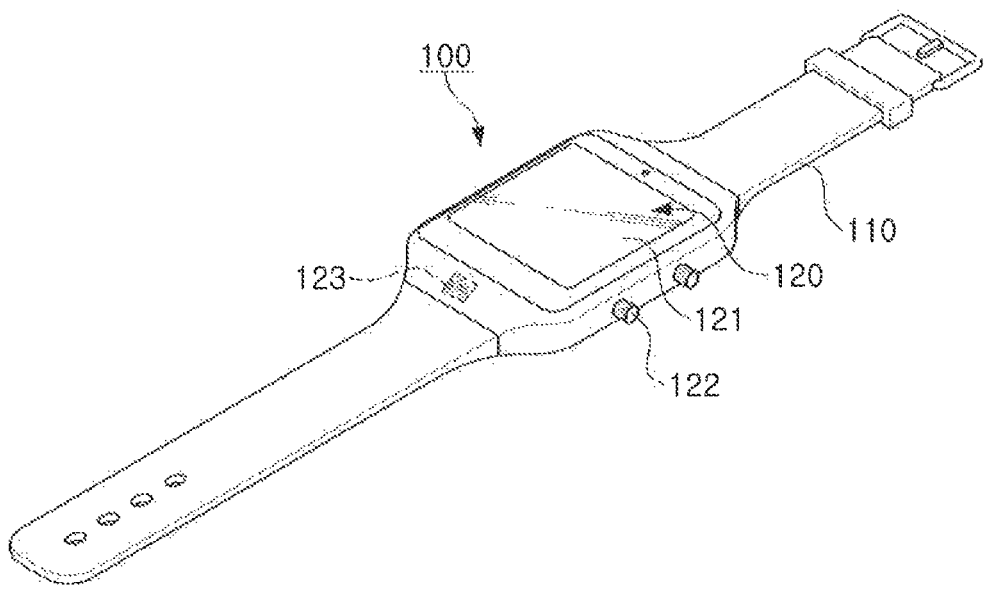
FIG. 2 is a perspective view of a front surface a wearable electronic device according to an example embodiment of the inventive concept.
Figure 3:
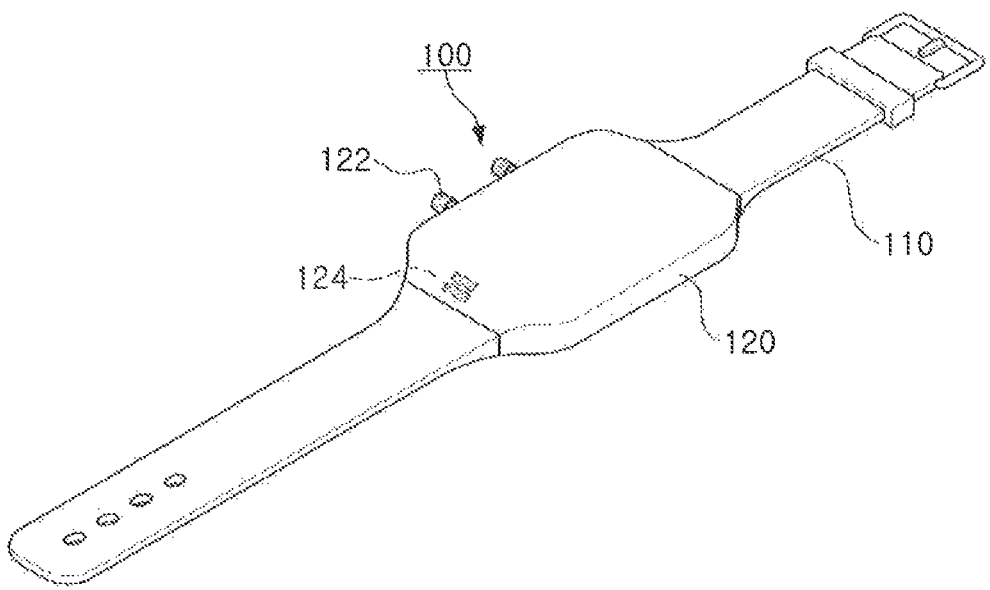
FIG. 3 is a perspective view of a rear surface of a wearable electronic device according to an example embodiment of the inventive concept.

FIGS. 1, 2 and 3 are views of a wearable electronic device according to an example embodiment of the inventive concept.

With reference to FIG. 1, a wearable electronic device 100 according to an example embodiment of the inventive concept may include a fixing part 110 for affixing the wearable electronic device 100 to a body of a user. The fixing part may include, but is not limited to a band, strap, etc. The wearable electronic device includes a body part 120 that may include a display 121, an input part 122, a first electrode part 123, etc. In the example embodiment illustrated in FIG. 1, the wearable electronic device 100 may be provided as a smartwatch. A person of ordinary skill in the art also understands the wearable electronic device could be manufactured and sold without a fixing part, which could be sold separately and attached to the body part. IT should also be understood and appreciated that the fixing part could also be a lanyard (e.g. for wearing the device as though it is a pendent), or even to attach the wearable electronic device to, for example, a decorative string or chain similar to a pocket watch.

The wearable electronic device 100 according to an example embodiment may include a biosensor that obtains biometric information of the user, by using body information and bioelectrical impedance of the user, or the like. The biosensor may measure, for example, the bioelectrical impedance of a user by applying a predetermined electrical signal to a body of the user when the user brings a part of their body into contact with the first electrode part 123. A predetermined electrical signal is applied to a body of the user, and an electric current and a voltage are detected. In an example embodiment, the first electrode part 123 may include, for example, a pair of electrodes, while the pair of electrodes may be disposed to be adjacent to each other. Thus, the user may be simultaneously in contact, with the pair of electrodes included in the first electrode part 123, using a single finger, thereby increasing user convenience in a process of measuring the bioelectrical impedance. In addition, a space of the wearable electronic device 100 having a limited form factor may be more efficiently used in such a manner when constructed such that the pair of electrodes (as in this example embodiment) are disposed to be adjacent to each other.

The biometric information of the user obtained by the biosensor of the wearable electronic device 100 may be output on the display 121 of the wearable electronic device 100 or may be output, to the user by an external electronic device (e.g. in this example a mobile device 10) connected to the wearable electronic device 100 to communicate therewith. In an example embodiment illustrated in FIG. 1, the mobile device 10 is illustrated as a mobile device, such as a smartphone and a tablet PC. In addition, the mobile device 10 shown in FIG. 1 may be substituted, with various types of devices, including but not in any way limited to, for example, a television, a refrigerator, a desktop computer, and exercise equipment.

According to an embodiment of the inventive concept, biometric information obtained by the biosensor of the wearable electronic device 100 may be stored and managed in a secure area of a memory included in the wearable electronic device 100. Biometric information, when obtained by unauthorized users, cannot be reset, such as a password, or credit card number. Accordingly, the security of such biometric information should be safeguarded, for example, by an authentication process. In an example embodiment, in a case in which an attempt to display the biometric information stored in the secure area on the display 121, or an attempt to share the biometric information with the mobile device 10 is detected, the wearable electronic device 100 or the mobile device 10 may provide the user with a predetermined authentication process. In other words, only when the user passes the authentication process, then may the biometric information ma displayed on the display 121, or may be shared with the mobile device 10, thereby allowing the biometric information to be safely stored and managed.

It is within the inventive concept to provide the user with a link that may be selected for the authentication process. For example, the link may be displayed on the wearable device, or it can be transmitted to the mobile device 10. Upon selecting the link, an authentication process may be executed that resides with the wearable device, or within the mobile device 10, or may be provided by an authenticated server. The user may respond to authentication prompts and/or addition biometric information such as an iris scan or fingerprint may be required to complete the authentication.

The mobile device 10 may include a housing 11, a display 12, a camera portion 13, a fingerprint sensor 14, and the like. In a case in which the user receives the biometric information through the mobile device 10, the user may have access authority to the biometric information stored in the wearable electronic device 100 by passing the authentication process, which may include one or more of the recognition of a fingerprint, input of a password and a pattern, recognition of an iris and a face, detection of em electrocardiogram (ECG) signal and an electromyogram (EMG) signal, or the like, provided by the mobile device 10 or the wearable electronic device 100. In an example embodiment, at least one of the authentication processes may be provided by the mobile device 10, while the other of the authentication processes may be provided by the wearable electronic device 100. In a case in which the authentication process, such as the detection of an ECG signal or an EMG signal, is provided entirely or primarily by the wearable electronic device 100, the user may perform the authentication process in such a manner that the user brings a part (e.g. a portion) of his/her body into contact with the pair of electrodes included in the first electrode part 123.

FIGS. 2 and 3 are perspective views of a front and a rear of a wearable electronic device 100 according to an example embodiment of the present inventive concept. With reference to FIGS. 2 and 3, a wearable electronic device 100 may include, for example, a fixing part 110 and a body part 120, while the body part 120 may include a display 121, an input part 122, a first electrode part 123, and a second electrode part 124. The wearable electronic device 100 is illustrated as a smartwatch, but may include various devices wearable on a body of a user, in addition to a smartwatch.

With reference to FIGS. 2 and 3, the body part 120 may have a first surface on which the display 121 is disposed and a second surface opposed thereto. In other words, the second surface may be provided as a surface with which skin of the user is in contact, when the user wears the wearable electronic device 100. The first surface may be provided as an outwardly exposed surface. The first electrode part 123 may be disposed on the first surface (e.g. FIG. 2), while the second electrode part 124 may be disposed on the second surface (e.g. FIG. 3). Each of the first electrode part 123 and the second, electrode part 124 may include a pair of electrodes. The pair of electrodes included in each of the first electrode part 123 and the second electrode part 124 may be disposed to be adjacent to each other.

As described above, a biosensor may be included in the body part 120 of the wearable electronic device 100. The biosensor may obtain various biometric information, such as fat mass, body mass index (BMI), muscle mass, total body water, fat mass index, and fat free mass index, by measuring, for example, bioelectrical impedance of the user. The biosensor may be mounted on a circuit board, while the circuit board may be electrically connected to electrodes included in the first electrode part 123 and the second electrode part 124. In a case in which the user wears the wearable electronic device 100 and brings a part of their body into contact with the first electrode part 123, the first electrode part 123 and the second electrode part 124 may simultaneously be in contact with a body of the user. For example, the second electrode part 124 may be in contact with the skin on the wrist of the user wearing the electronic device, and a finger of the user may touch the first electrode part 123 of the wearable device. While the first electrode part 123 and the second electrode part 124 are simultaneously in contact with the body of the user, the biosensor may apply an electrical signal thereto through the first electrode part 123 and the second electrode part 124, thereby measuring bioelectrical impedance of the user.

In a case in which, for example, the wearable electronic device 100 is provided as a smartwatch, the user may wear the wearable electronic device 100 on his wrist. A human's wrist has a curved form. Thus, in a case in which, the first electrode part 123 and the second electrode part 124 are not appropriately designed, the second electrode part 124 may be detached from the body of the user by an operation in which the body of the user is in contact with the first electrode part 123. In an example embodiment, the first electrode part 123 and the second electrode part 124 may be disposed to face each other so that the first electrode part 123 and the second electrode part 124 may be simultaneously in contact with the body of the user. If it within the inventive concept that the first electrode part 123 and the second electrode part can be arranged on the same surface, or different surfaces of the wearable device according to need.

In the meantime, in the example embodiments illustrated in FIGS. 1 to 3, the electrodes included in the first electrode part 123 and the second electrode part 124 are illustrated as having a rectangular shape, but the shapes of the electrode are not limited thereto. In addition, the electrodes included in the respective first electrode part 123 and the second electrode part 124 can have respectively different shapes and sizes. Hereinafter, an example embodiment will be described with reference to FIGS. 4A and 4B.

Figure 4A:
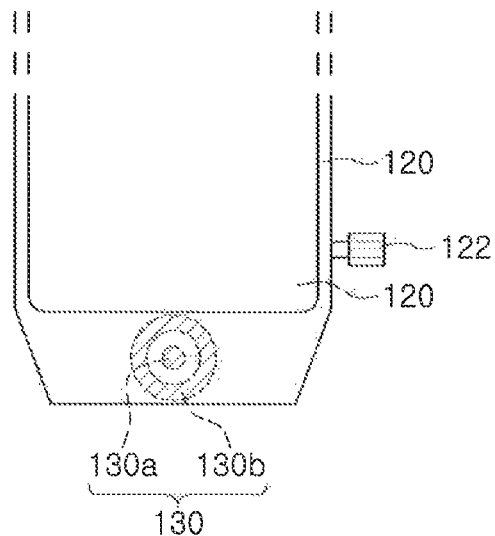
FIG. 4A illustrates an embodiment of a wearable electronic device according to an example embodiment in which a pair of electrodes has a concentric shape.
Figure 4B:
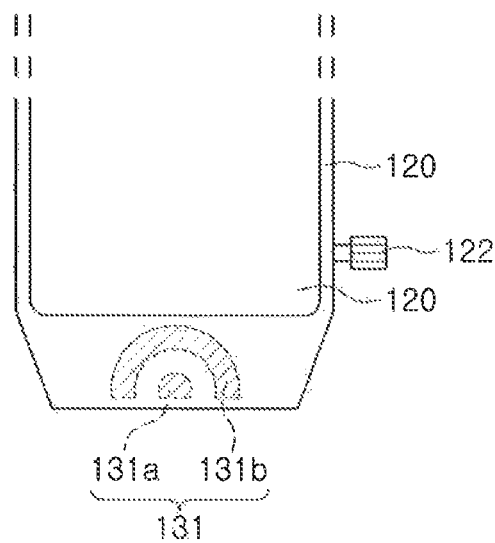
FIG. 4B illustrates an arrangement of electrodes of a wearable electronic device having a semi-circular shape according to an example embodiment of the inventive concept.

FIGS. 4A and 4B are views illustrating an arrangement of electrodes of a wearable electronic device according to an example embodiment of the inventive concept.

With reference to FIG. 4A, a wearable electronic device 100A according to an example embodiment may include a body part 120, a display 121, an input part 122, and the like. A first electrode part 130 may be disposed on a side of a first surface defined as an upper surface of the body part 120. The first electrode part 130 may include a pair of electrodes 130a and 130b.

In the example embodiment illustrated in FIG. 4A, the pair of electrodes 130a and 130b may have a concentric shape, but the inventive concept is not limited to this depiction. The user may bring a part of their body, for example, a finger, into contact with the first electrode part 130, thereby allowing the body part to be simultaneously in contact with the pair of electrodes 130a and 130b.

Subsequently, with reference to FIG. 4B, a first electrode part 131 included in a wearable electronic, device 100B according to an example embodiment may include a pair of electrodes 131a and 131b. The pair of electrodes 131a and 131b shown in FIG. 4B may include an internal electrode 131a and an external electrode 131b, while the external electrode 131b may have a semicircular shape surrounding the internal electrode 131a. The user may bring a part of their body, such as a finger, into contact with the first electrode part 131, thereby allowing his body to be simultaneously in contact with the pair of electrodes 131a and 131b. A person of ordinary skill in the art should also understand and appreciate that the internal electrode 131a and the internal electrode 131b are not limited to corresponding shapes. For example, according to the inventive concept, the external electrode 131b may be semicircular in shape, and the internal electrode 131a may be circular, rectangular, or have an irregular shape.

Figure 5:
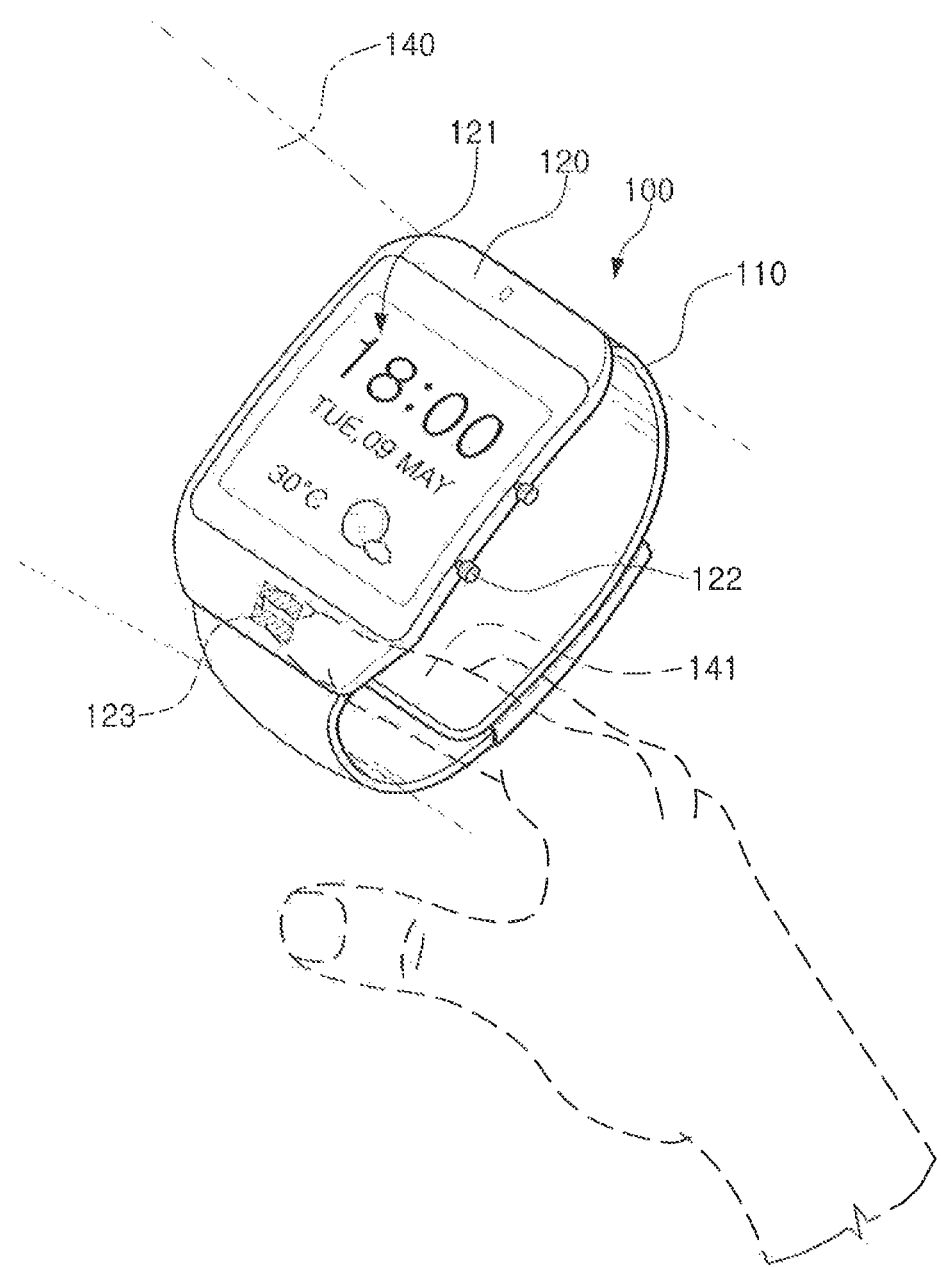
FIG. 5 is a view illustrating an operation of a wearable electronic device being operated by a user, according to an example embodiment of the inventive concept.

FIG. 5 is a view illustrating an operation of a wearable electronic device according to an example embodiment. It should be understood by a person of ordinary skill in the art that the inventive concept is not limited to devices worn on the wrist, and for example, could be worn on an ankle a finger, attached to a lanyard and worn as a pedant, or may be temporarily affixed to the skin, for example, via an adhesive. The wearable electronic device may also be attached to a user's article of clothing, which may have a predetermined opening or base by which the wearable electronic device is detachably connected.

In the example embodiment illustrated in FIG. 5, a wearable electronic device 100 is illustrated as a smartwatch, but may be changed into devices having various other forms that a user may wear on his body, in addition thereto. With reference to FIG. 5, the user may wear the wearable electronic device 100 on a wrist 140. The wearable electronic device 100 may be fixed to the wrist 140 of the user by a fixing part 110 provided to have a strap form. It is also within the inventive concept, that the fixing part could contain one or more electrodes. For example, the fixing part could have an electrode in the portion of the strap that is in contact with the user's wrist, and there may be an internal conductive channel with an interface that is electrically connected to a port of the wearable device.

A body part 120 may have a first surface on which a display 121 and a first electrode part 123 are disposed and a second surface opposed thereto. A second electrode part may be disposed on the second surface. In an example embodiment, the second electrode part 124 (FIG. 6B), may be disposed in a position of opposing the first electrode part 123, e.g., below the first electrode part 123.

With continued reference to FIG. 5, in a case in which biometric information is measured using the wearable electronic device 100, the user may bring a finger 141 into contact with the first electrode part 123. The user may bring the finger 141 into contact with the first electrode part 123, so that the finger 141 may be simultaneously in contact with a pair of electrodes included in the first electrode part 123. In addition, the second electrode part 124 disposed below the first electrode part 123 may be in contact with skin on the wrist 140 of the user by an operation in which the first electrode part 123 is pressed using the finger 141. Thus, while the wearable electronic device 100 measures bioelectrical impedance of the user, an entirety of the first electrode part 123 and the second electrode part may be in stable contact with a body of the user.

The inventive concept as embodied in the example of FIG. 5 may have a function of measuring biometric information in which, for example, the wearable electronic device 100 may obtain the biometric information only by an operation in which the user brings a finger 141 into contact with the first electrode part 123. In a method of the related art, there are two fingers in contact with two electrodes disposed to be spaced apart from each other, and a resistance component present in each of the two fingers may be naturally offset. On the other hand, in the case of the wearable electronic device 100 according to an example embodiment, the finger 141 may be in simultaneous contact, with the pair of electrodes included in the first electrode part 123, so that a circuit, a software algorithm, or the like, which compensates for the resistance component of the finger 141, may be disposed in the wearable electronic device 100.

In an example embodiment, the first electrode part 123 may be provided as an electrode for detecting a fingerprint of the user. In a case in which the fingerprint of the user is detected from, the first electrode part 123, a biosensor in the wearable electronic device may measure bioelectrical impedance of the user, and obtain the biometric information of the user.

Figure 6A:
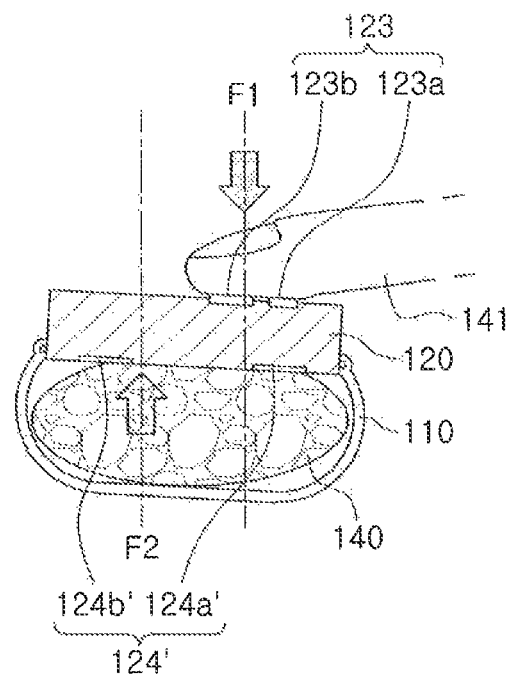
FIG. 6A illustrates a first surface of the wearable electronic device being provided as an outwardly exposed surface.
Figure 6B:
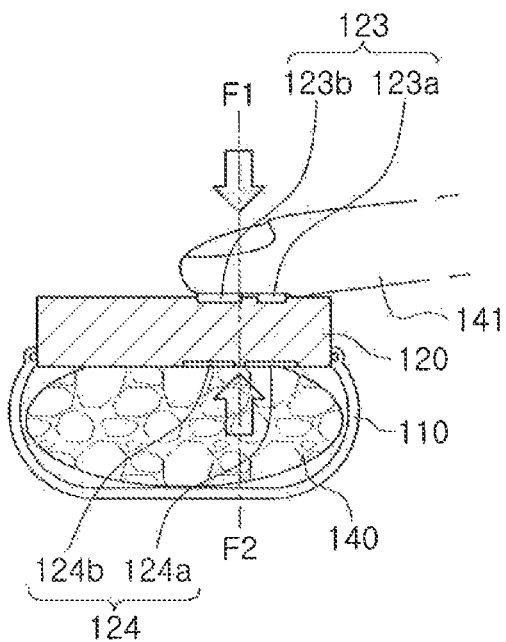
FIG. 6B illustrates a process in which the electrodes of a wearable electronic device according to an example embodiment of the inventive concept are in contact with a body of a user.

FIGS. 6A and 6B are views illustrating an embodiment of a process of the inventive concept, in which electrodes of a wearable electronic device are in contact with a body of a user.

With reference to FIG. 6A, the wearable electronic device may include a fixing part 110 and a body part 120. The body part 120 may include a first electrode part 123 disposed on a first surface of the body part 120 and a second electrode part 124' disposed on a second surface of the body part 120. The first surface may be provided as an outwardly exposed surface while the user wears the wearable electronic device. The second surface may be provided as a surface opposed thereto. In an example embodiment illustrated in FIG. 6A, the first electrode part 123 may include a pair of electrodes 123a and 123b disposed to be adjacent to each other on a side of the first surface. On the other hand, a pair of electrodes 124a' and 124b' included in the second electrode part 124' may be disposed to be spaced apart from each other on the second surface. Thus, the space between the pair of electrodes 132a, 123b is different from, (and in this case less than) the space between the [air of electrodes 124a' and 124b'.

In a case in which the user presses the pair of electrodes 123a and 123b included in the first electrode part 123, using a body part, such as a finger 141, a biosensor of the wearable electronic device may measure the bioelectrical impedance of the user. In an example embodiment, while the biosensor measures the bioelectrical impedance, the first electrode part 123 and the second electrode part 124' shown in FIG. 6A may be simultaneously in contact with, the body of the user. In an example embodiment illustrated in FIG. 6A, second force F2 may be generated in an opposite direction by first force F1 that the user applies to the first electrode part 123. The first force F1 may cause the body part 120 to slightly tilt such that at least one of the pair of electrodes 121a' and 124b' included in the second electrode part 124' may be detached from the body of the user by the second force F2. Thus, the bioelectrical impedance of the user may not be accurately measured, or an error may occur in a measurement process.

With reference to FIG. 6B, in an example embodiment of the inventive concept, in the same manner as the first electrode part 123, a second electrode part 124 may be disposed on a side of the second surface, which may enhance the accuracy of the bioelectrical impedance measured by the wearable electronic device. With reference to FIG. 6B, the second force F2 applied between the second electrode part 124 and a wrist 140 of the user may be generated by the first force F1 that the user applies to the first electrode part 123 using the finger 141. However, in a manner different from a case illustrated in FIG. 6A, a pair of electrodes 124a and 124b included in the second electrode part 124 may be disposed to be adjacent, to each other below the first electrode part 123. Thus, in the structural arrangement shown in FIG. 6B, the first force F1 and the second force F2 may be generated in the substantially same position. Due to the position of the second force F2 shown in FIG. 6B, the pair of electrodes 124a and 124b included in the second electrode part 124 may be in stable contact with the wrist 140 of the user.

Figure 7:
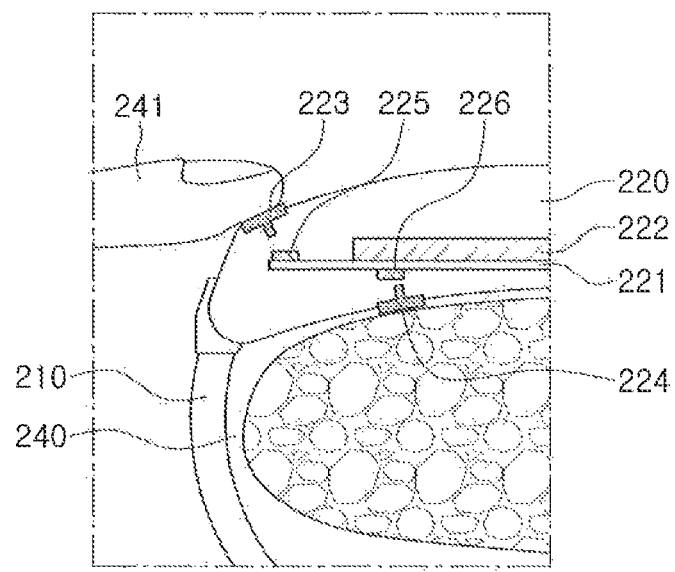
FIG. 7 illustrates a wearable electronic device including a fixing part and a body part of the inventive concept.
Figure 8:
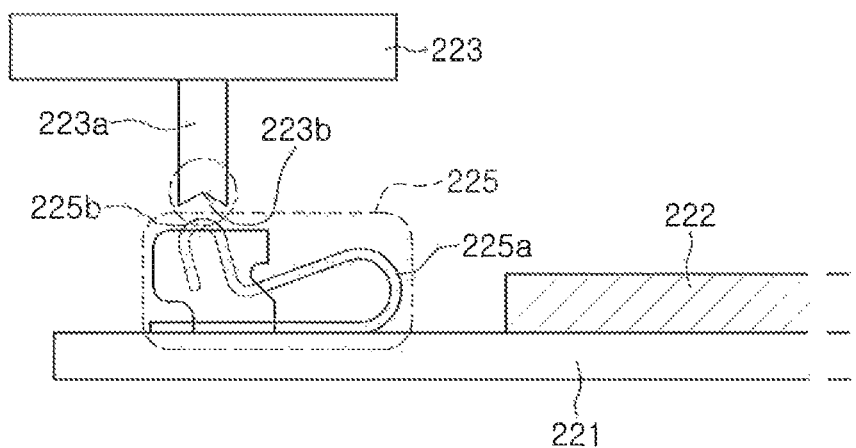
FIG. 8 illustrates the operation of a wearable electronic device according to an example embodiment of the inventive concept.

FIGS. 7 and 8 are views illustrating an operation of the wearable electronic device according to an example embodiment of the inventive concept.

With reference to FIG. 7, the wearable electronic device may include a fixing part 210 and a body part 220. In the body part 220, a circuit board 221 including a biosensor 222 mounted thereon may be disposed. The biosensor 222 may be provided as an integrated circuit chip package to be mounted on the circuit board 221. On the circuit board 221, a memory, an application process, and the like, may be mounted together, in addition to the biosensor 222.

With continued, reference to FIG. 7, the user may bring a part of his/her body, such as a finger 241, into contact with a first electrode part 223 disposed on a first surface of the body part 220 of the wearable electronic device, so that the biosensor 222 may measure the bioelectrical impedance of the user. On an opposite side of the first electrode part 223, a second electrode part 224 may be disposed on a second surface of the body part 220. In a case in which the user presses the first electrode part 223 using their finger 241, the second electrode part 224 may be in contact (or may come into contact) with a wrist 240 of the user by the force applied to the first electrode part 223 by the finger 241.

According to an example embodiment of the inventive concept illustrated in FIG. 7, the electrodes respectively included in each of the first electrode part 223 and the second electrode part 224 may include a connection portion protruding toward a circuit board. The circuit board 221 may include, for example, contact parts 225 and 226 that are conductive. The contact parts 225 and 226 may electrically connect with a respective connection portion of the first electrode part 223 and the second, electrode part 224 by force the user applies to the first electrode part 223. For example, the connection portion of the first electrode part 223 may form an electrical connection with the contact part 225, and the second, electrode part 224 may form an electrical connection with contact part 226 when the finger 241 applies sufficient force to the first electrode. The biosensor 222 may apply an electrical signal to each of the first electrode part 223 and the second electrode part 224 through the contact parts 225 and 226 and may detect an electric current and a voltage to measure the bioelectrical impedance of the user. Hereinafter, with reference to FIG. 8, structures of the first electrode part 223, the second electrode part 224, and the contact parts 225 and 226 will be described in more detail.

With reference to FIG. 8, an electrode included in the first electrode part 223 may include a connection part 223a of the first electrode part 223 protruding toward the circuit board 221. More particularly, the connection part 223a of the first, electrode part 223 may be arranged to protrude toward the contact part 225 of the circuit board 221 so as to be connectable with regard to the contact part. A concave portion 223b may be disposed on an end of the connection part 223a. The connection part 223a may electrically connect to the contact part 225 disposed on the circuit board 221 by an operation in which the user presses the first electrode part 223. The contact part 225 may include an elastic member 225a that offsets the force applied when being in contact with the first electrode part 223 and may include a protruding portion 225b connected to the elastic member 225a. In an example embodiment, the protruding portion 225b of the contact part 225 may become interlocked with the concave portion 223b of the first electrode part 223 upon application of a force to the first electrode part, so that the first electrode part 223 is connected to the contact part 225 to apply an electrical signal, such as an electric current and a voltage. Structures of the first electrode part 223 and the contact part 225 that have been described with reference to FIG. 8 may be similarly applied, to the second electrode part 224 and a contact part 226.

Figure 9:
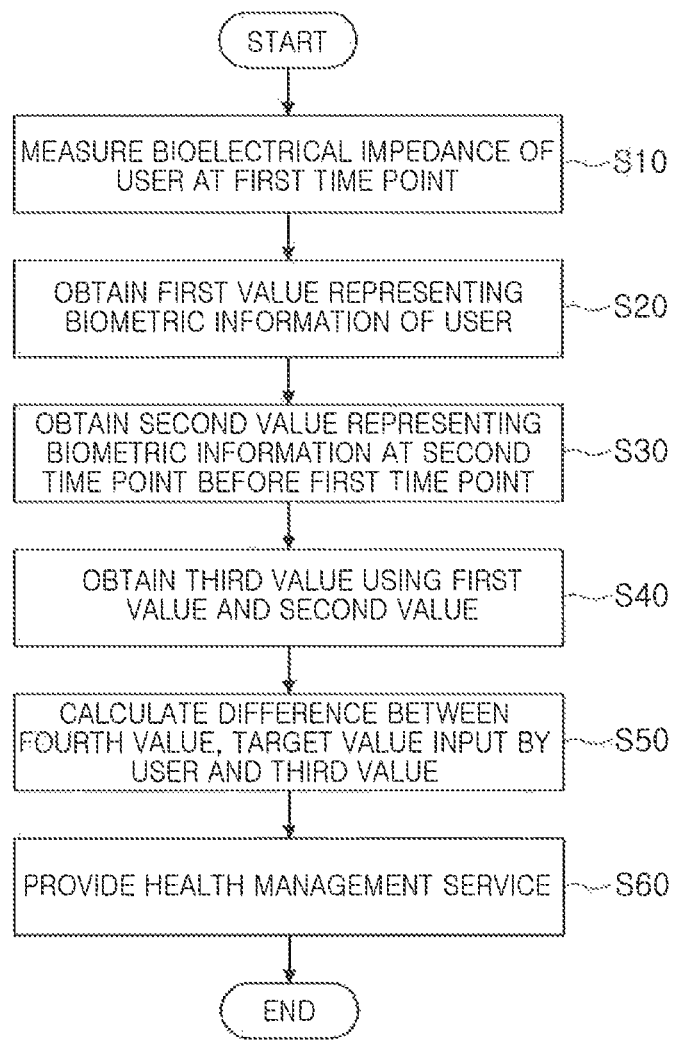
FIG. 9 is a flowchart illustrating a method of providing a service according to an example embodiment of the inventive concept.

FIG. 9 is a flowchart illustrating a method of providing a service according to an example embodiment of the inventive concept. In an example embodiment, the method, of providing a service described with reference to a flowchart; illustrated in FIG. 9 may be implemented by a biometric information measuring device that is configured to include a function of measuring biometric information, or by other electronic devices connected, to the biometric information measuring device to be able to communicate therewith.

With reference to FIG. 9, the method of providing a service according to an example embodiment may begin at operation S10 by measuring bioelectrical impedance of a user at a first time point. In the method of providing a service according to an example embodiment, when the electrodes of the biometric information measuring device is in contact with a body of the user, an electrical signal may be applied to the body of the user, and an electric current and a voltage may be detected, thereby measuring bioelectrical impedance.

According to the method of providing a service according to an example embodiment, at operation S20 a first value representing specific bioelectrical impedance of the user may be obtained. The first value may foe provided as biometric information calculated from bioelectrical impedance measured at a first time point, body information input by the user, and the like. In other words, the first value may be provided as a value representing biometric information at the first time point. Body information input by the user to calculate the first value may include, for example, race, gender, age, height, body weight, and the like. In an example embodiment, the first value may be provided as a value representing at least one of fat mass, BMI, muscle mass, total body water, fat mass index, and fat free mass index, included in biometric information of the user.

At operation S300, in a case in which the first value has been calculated, the second value representing biometric information at a second time point before (e.g. prior to) the first time point may be obtained. The second value may be provided as a value that was obtained earlier in time than the first time point. For example, as the second time point has already passed, the second value representing biometric information at the second time point may have been stored in a memory, or the like.

With continued reference to the flowchart in FIG. 9, at operation S40 the biometric information measuring device, or an electronic device connected to the biometric information measuring device that is able to communicate therewith, may obtain a third value representing biometric information at a third time point that occurs after the first time point, by using the first value and the second value. In an example embodiment, the third value calculated in operation 340 may be provided as a value to predict any change among pieces of biometric information of the user.

At operation S50, in a case in which the third value is calculated, a difference between a fourth value and the third value may be calculated. The fourth value may be a target value input by the user in advance.

At operation S50, based on the difference between the third, value and the fourth value, a health management service may be provided. In other words, according to the method of providing a service described with reference to the flowchart illustrated in FIG. 9, a trend may be analyzed based on the first value representing a present state of biometric information of the user and the second value representing a past state of the biometric information. According to the inventive concept, the third value, which predicts a future state of the biometric information based on the past state and the present state, may be calculated based thereon. According to the method of providing a service according to an example embodiment, the difference between the fourth value, a target value of the biometric information input by the user in advance and the third value may be calculated. Based on the difference, a diet management service, an exercise guidance service, or the like, utilized to achieve goals may be provided to the user.

In an example embodiment of the inventive concept, the first value, the second value, the third value, and the fourth value, representing specific biometric information of the user may be managed by being linked to identity information of the user. For example, identity information of the user may include information such as a name input by the user in advance and an authentication process set by the user in advance. In other words, in a case in which the authentication process set by the user in advance is not successful, the health management, service based on the first value, the second value, the third value, and the fourth value may not be provided (see operation S60 in FIG. 9). Thus, biometric information including sensitive personal information of the user may be more securely managed.

Figure 10:
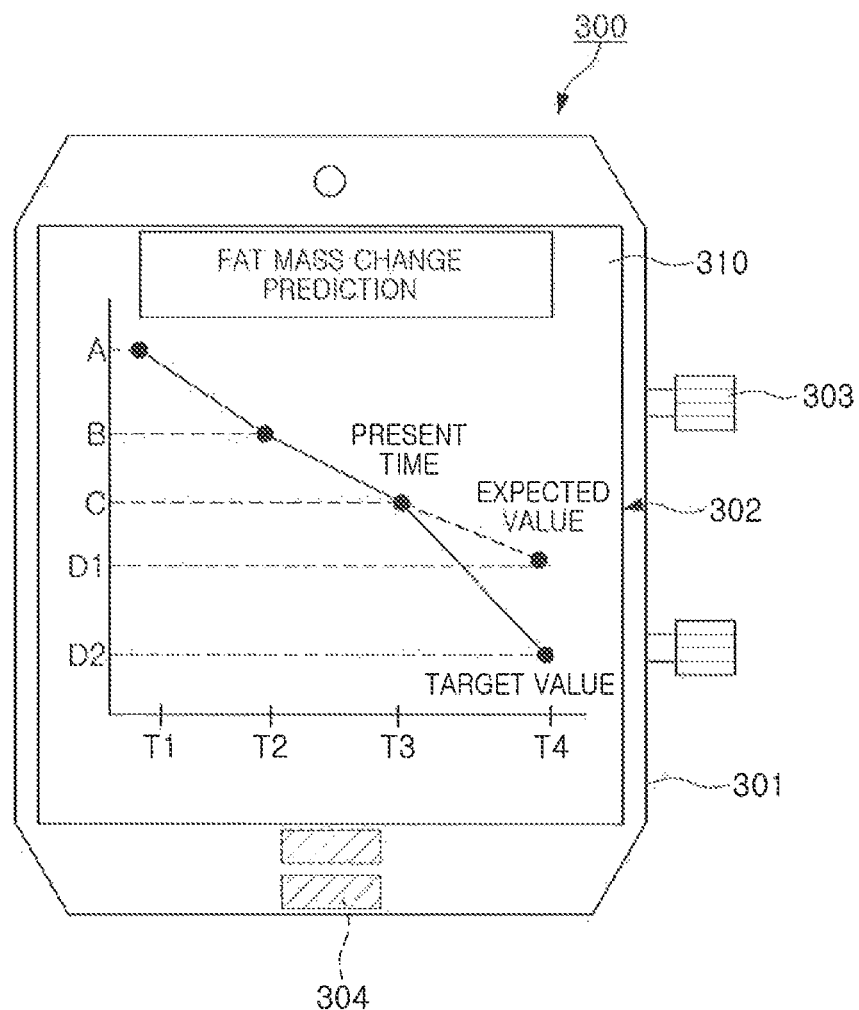
FIG. 10 illustrates a method of providing a service according to an example embodiment of the inventive concept.
Figure 11:
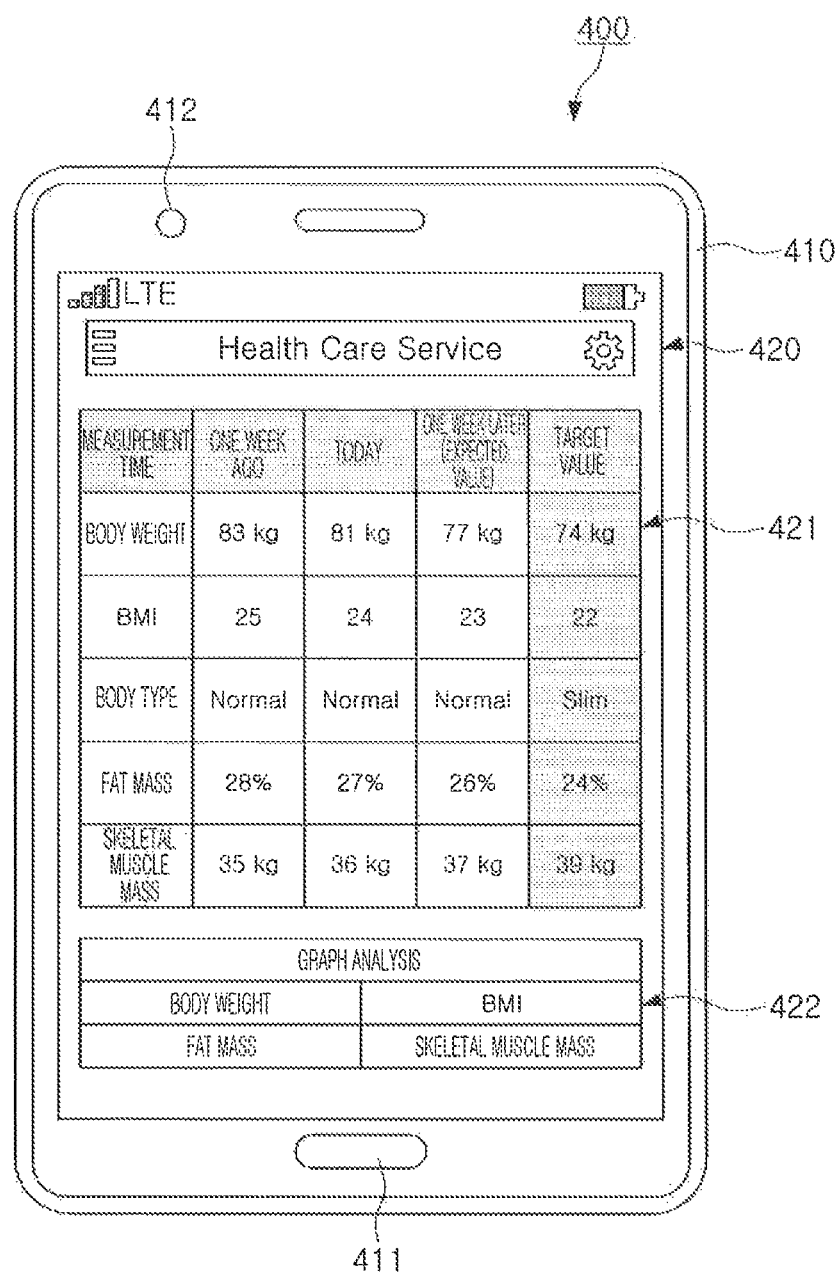
FIG. 11 illustrates a change prediction service regarding a range of biometric information displayed by a mobile device.
Figure 12:
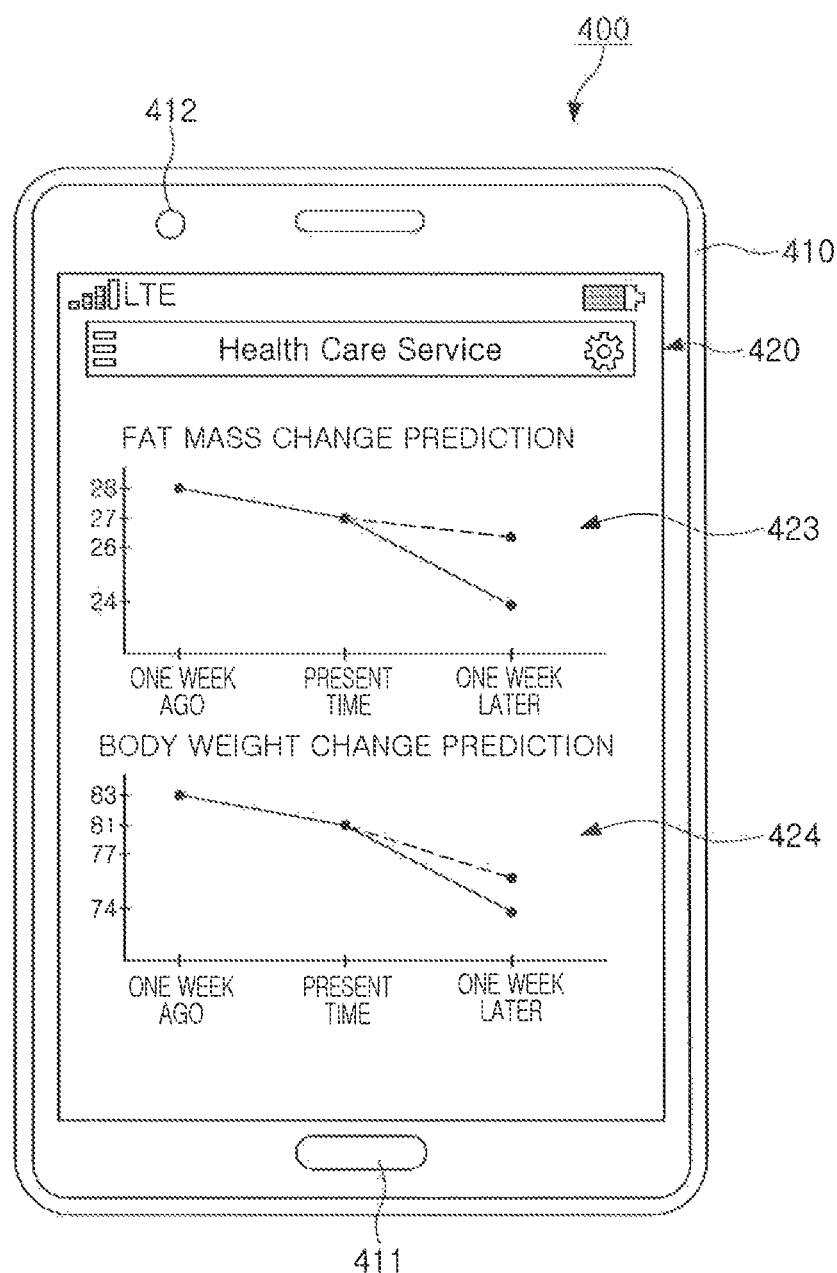
FIG. 12 illustrates a health care service displayed by a mobile device.

FIGS. 10, 11 and 12 are views illustrating a method of providing a service according to an example embodiment.

With reference to FIG. 10, the method of providing a service according to an example embodiment may be provided by a wearable electronic device 300. The wearable electronic device 300 may include a body part 301. In the body part 301, a display 302, an input part 303, an electrode part 304, and the like, may be provided. In a case in which a user wears the wearable electronic device 300 and brings a part of the user's body into contact with the electrode part 304, the wearable electronic device 300 may measure bioelectrical impedance of the user.

A health management service provided in an example embodiment illustrated in FIG. 10 may include a fat mass change prediction service. On a service screen 310, a graph illustrating fat mass values A, B, C, D1, and D2 in each of a plurality of instances T1, T2, T3, and T4 may be displayed. In the example embodiment illustrated in FIG. 10, during a period from a first instance T1 representing an earliest instance to a third instance T3 representing a present instance, the fat mass change may be gradually reduced.

More particularly, in this embodiment of the inventive concept, the wearable electronic device 300 may predict a changing fat mass trend using fat mass values A and B obtained in each of the first time point T1 and a second time point T2, representing the past, and a fat mass value C obtained in the third time point T3 representing the present. With reference to FIG. 10, an expected fat mass value D1 calculated from the changing trend of fat mass may be displayed on the graph. In detail, the expected fat mass value D1 may be displayed together with a target fat mass value D2 input by the user in advance, in the graph. Information that can be used to reduce a difference between the expected fat mass value D1 and the target fat mass value D2 together with the graph may be provided to the user. In an example embodiment, the information may include a diet information service for the sake of the user, an exercise guidance service, a recommended calorie consumption information service, and the like, required by the user.

Subsequently, with reference to FIG. 11, a change prediction service regarding a range of biometric information, such as body weight, BMI, body type, fat mass, skeletal muscle mass, or the like, may be provided by the method of providing a service according to an example embodiment of the inventive concept. With reference to FIG. 11, a change prediction service of biometric information may be provided by an electronic device 400 having a function of measuring biometric information, or there may be change prediction service that is in communication with a biometric information measuring device to be able to communicate therewith.

The electronic device 400 may include a housing 410, a fingerprint sensor 411, a camera part 412, and the like. A service screen 420 disposed on a display of the electronic device 400 may include a table 421 in which a past value, a present value, an expected value, and a target value of a plurality of biometric information parameters are displayed together. A person of ordinary skill in the art understands and appreciates that the table 421 is provided for illustrative purposes, and the inventive concept is not limited to displaying the types of items shown in the table 421. The table 421 may display more parameters or fewer parameters than shown and while this table may be initially set as a default, the user, manufacturer of the wearable device, or the service prediction provider may update or change the items displayed in table 421.

In an example embodiment, of the inventive concept, the target value of at least one of the parameters displayed in the table 421 may be provided as a value inversely calculated from a target value pf a different parameter set by the user. In detail, in a case in which the user inputs only the target values of fat mass and skeletal muscle mass, the electronic device 400 may calculate a target body weight value using a target fat mass value and a target skeletal muscle mass value input by the user. In a case in which the user inputs the target value of only a parameter calculated using a specific operation process, such as fat mass, skeletal muscle mass, BMI, and body type, the user may calculate the target value of a parameter easily discernible by the user from target values input by the user, thereby providing a more intuitive health management service. In an example embodiment of the inventive concept, in a case in which a parameter most discernible to the user is body weight, and the body weight of the user reaches 74 kg, a target value, the user may determine that fat mass and skeletal muscle mass has reached a value close to a target, value set by the user.

With continued reference to FIG. 11, the service screen 420 may provide a graph analysis service 422 on a bottom portion thereof. In a case in which the user selects one or more parameters among parameters included in the graph analysis service 422, the electronic device 400 may produce a graph of a selected parameter to be displayed. Hereinafter, an example embodiment will be described with reference to FIG. 12. A person of ordinary skill in the art understands that the graph analysis service may be displayed in a various ways, and could be displayed, for example, in response to a user touch, voice command, icon selection, etc, FIG. 12 illustrates an example embodiment in which the user has selected the fat mass and body weight in the graph analysis service 422 such as shown in FIG. 11. With reference to the service screen 420 displayed in the electronic, device 400, a first graph 423 predicting a changing trend of fat mass and a second graph 424 predicting a changing trend of body weight may be displayed. In each of the first graph 423 and the second graph 424, target values of fat mass and body weight may be displayed together.

In the example embodiment illustrated in FIG. 12, in a case where the user maintains a current lifestyle, information that the target values of fat mass and body weight may not achieved may be confirmed in the first graph 423 and the second graph 424. Thus, with reference to the table 421 and graphs 423 and 424 provided by the service screen 420, lifestyle, such as diet and an amount of exercise may be modified and supplemented. In an example embodiment, the electronic device 400 may provide information about diet and the amount of exercise to permit reaching a target value input by the user in advance and may provide the information to the user.

Figure 13:
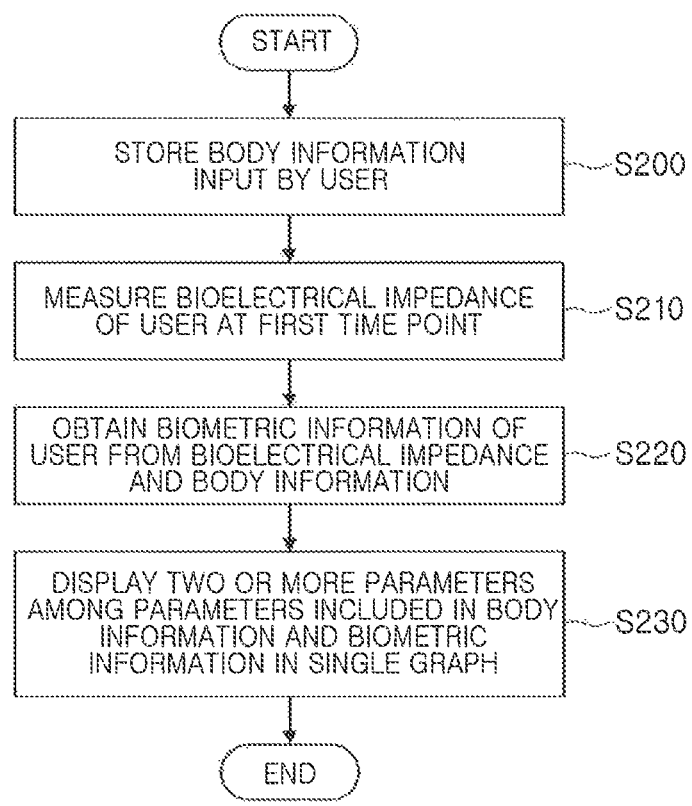
FIG. 13 is a flowchart illustrating a method of providing a service according to an example embodiment of the inventive concept.

FIG. 13 is a flowchart illustrating a method of providing a service according to an example embodiment of the inventive concept.

With reference to FIG. 13, in operation S200 the method of providing a service according to an example embodiment, may be started by storing body information input by a user.

The body information input by the user in S200 may include height, body weight, and the like, of the user. The user may input also input information, such as an age, race, and gender, in addition to height and body weight.

At operation S210, in a case in which the body information is input, bioelectrical impedance of the user may be measured at a first time. Bioelectrical impedance may be measured such that a predetermined electrical signal is applied through electrodes in contact with a body of the user, and an electric current and a voltage is detected. In a case in which bioelectrical impedance is measured, biometric information of the user may be obtained using body information input by the user in S200 and bioelectrical impedance in operation S220. The biometric information obtained in operation S220 may include fat mass, total body water, skeletal muscle mass, BMI, body type, and the like.

At operation S230, in a case in which the body information is obtained, the method of providing a service according to an example embodiment, may display two or more parameters among parameters included in body information and biometric information in a single graph in S230. In other words, among parameters included in body information, such as height and body weight, and parameters included in biometric information, such as fat mass, total body water, skeletal muscle mass, BMI, and body type, a plurality of parameters may be selected to be displayed as a single graph. In an example embodiment, a single graph displayed in S230 may include a plurality of axes illustrating the plurality of parameters.

The body type among the parameters included in the biometric information may be determined based on, for example, BMI calculated from height and body weight of the user and fat mass calculated from bioelectrical impedance of the user. Since the body type may be determined by more than a relationship between height and body weight, and may also be determined by a percentage of fat mass by weight, in an example embodiment, the body type of the user may be determined in full consideration of BMI and fat mass. Hereinafter, an example embodiment will be described herein below with reference to FIGS. 14 and 15.

Figure 14:
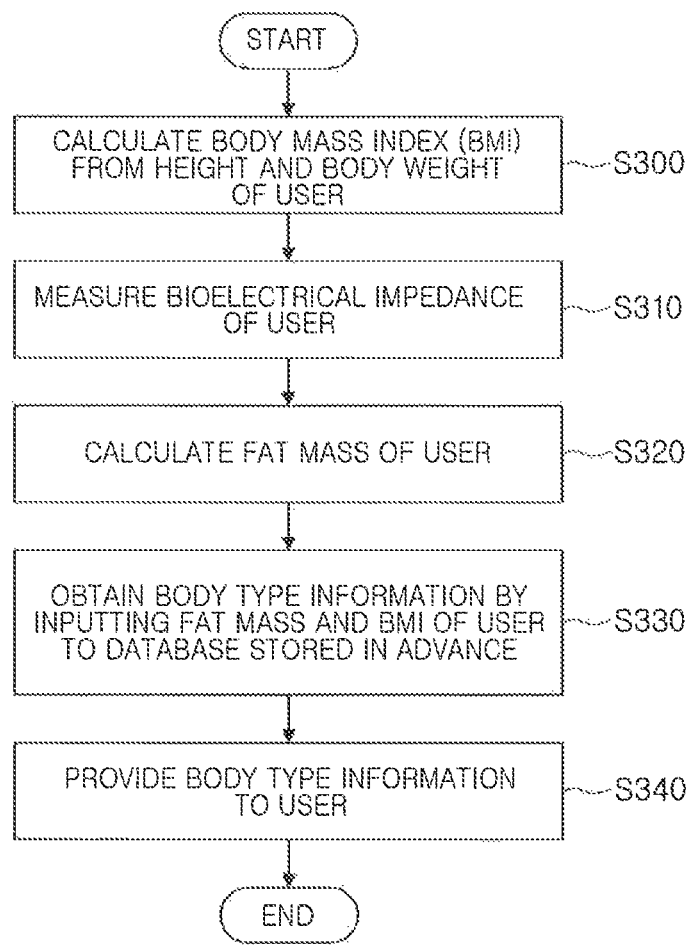
FIG. 14 is a flowchart illustrating a method of providing body type information in a method of providing a service according to an example embodiment of the inventive concept.
Figure 15:
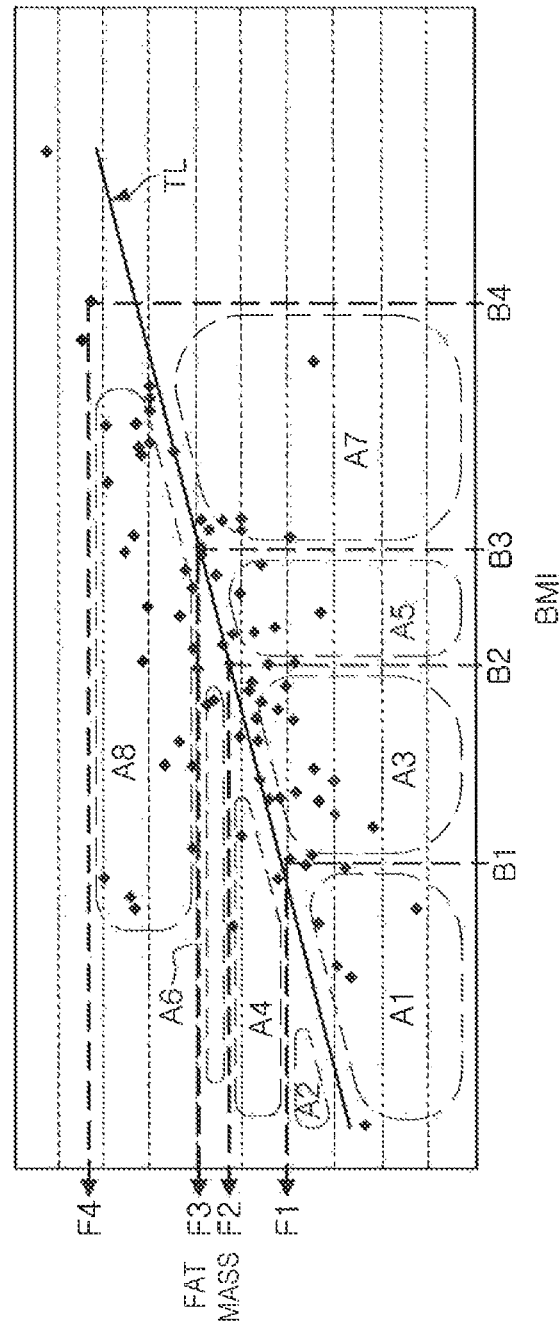
FIG. 15 is a graph illustrating a method of providing body type information in a method of providing a service according to an example embodiment.

FIG. 14 is a flowchart illustrating a method of providing body type information in a method of providing a service according to an example embodiment, while FIG. 15 is a graph illustrating the method of providing body type information in a method of providing a service according to an example embodiment.

With reference to FIG. 14, at operation S300, the method of providing body type information according to an example embodiment may be started by calculating BMI based on height and body weight of a user. The height and the weight of the user may be provided as a value directly input by the user. A different calculation method of calculating BMI may be applied depending on an age, gender, or the like, of the user.

At operation S310, in a case in which BMI is calculated, bioelectrical impedance of the user may be measured. The bioelectrical impedance of the user may be measured in such a manner that an electrical signal is applied through electrodes in contact with a body of the user, and an electric current and a voltage is detected through the electrodes.

At operation S320, the bioelectrical impedance that has been measured may be used in calculating fat mass, together with body information, such as the height and the weight, previously input by the user in operation S300.

In a case in which a BMI and a fat mass of the user are calculated, at operation S330, the BMI and the fat mass of the user may be input to a database already stored, thereby obtaining body information of the user. The database may include information in which body type information of the user is classified depending on BMI and fat mass.

At operation S340, the body type information provided in S330 may be provided to the user in S340. In an example embodiment, body information may be provided to be schematized as a single graph, together with other information, such as fat mass, body weight, BMI, total body water, and muscle mass of the user.

FIG. 15 is a graph illustrating the method of providing body type information. FIG. 15 is a graph illustrating the method of providing body type information of the user using BMI and fat mass as an example. A database required in providing the body type information may be stored to have a format different from that of FIG. 15.

With reference to FIG. 15, a horizontal axis may refer to BMI, while a vertical axis may refer to fat mass. In order to provide the body type information, a combination of BMI-fat mass of a number of people may be stored in a database and may be schematized on a graph, as illustrated in FIG. 15, thereby schematically determining a trend line TL. In an example embodiment of the inventive concept, the database displayed on the graph of FIG. 15 may vary depending on race, an age, gender, or the like, of the user.

In an example embodiment, a classification standard of body type information of the user may be provided using a body type standard based on BMI provided by the World Health Organization (WHO) and the trend line TL displayed on the graph. The body type standard based on BMI provided by WHO is illustrated in Table 1 below

TABLE 1

| Classification Standard Based on BMI | |
|---|---|
| Classification of Body Type | BMI |
| Underweight | ~18.5 |
| Normal Range | 18.5~24.9 |
| Overweight - Brink of Obesity | 25.0~29.9 |
| Obese        Class I | 30.0~34.9 |
|              Class II | 35.0~39.9 |
|              Class III | 40.0~ |

With reference to the graph of FIG. 15 and Table 1 above, boundary values of BMI determining classification of body type are displayed on the horizontal axis of the graph of FIG. 15. Four reference values B1 to B4 displayed on the horizontal axis of the graph of FIG. 15 may be 18.5, 25.0, 30.0, and 40.0 in. sequence. In the meantime, reference values F1 to F4 classifying fat mass on the graph of FIG. 15 may be determined by reference values B1 to B4 of BMI in a combination of BMI-fat mass included in the database. With reference to FIG. 15, at least eight pieces of body type information may be determined by the reference values B1 to B4 of BMI, the reference values F1 to F4 of fat mass, and the trend line TL.

With continued reference to FIG. 15, for example, a first area A1 may be defined as an underweight-low fat body type in which body weight is relatively light, as compared with height, and fat mass is relatively low. In the meantime, a second area A2 may be defined as a thin-obese body type in which body weight is relatively light, as compared with height, but fat mass is relatively high. In other words, a case in which an area is disposed below the trend line TL may be construed as a body type in which an amount of fat is low, as compared with body weight. A case in which an area is above the trend line TL may be construed as a body type in which the amount of fat is high, as compared with body weight.

In the method of providing a service according to an example embodiment, various parameters included in body information and biometric information and body type information obtained using a method described with reference to FIGS. 14 and 15 may be schematized as a single graph, thereby being provided to the user. Hereinafter, an example embodiment will be described with reference to FIGS. 16 to 18.

Figure 16:
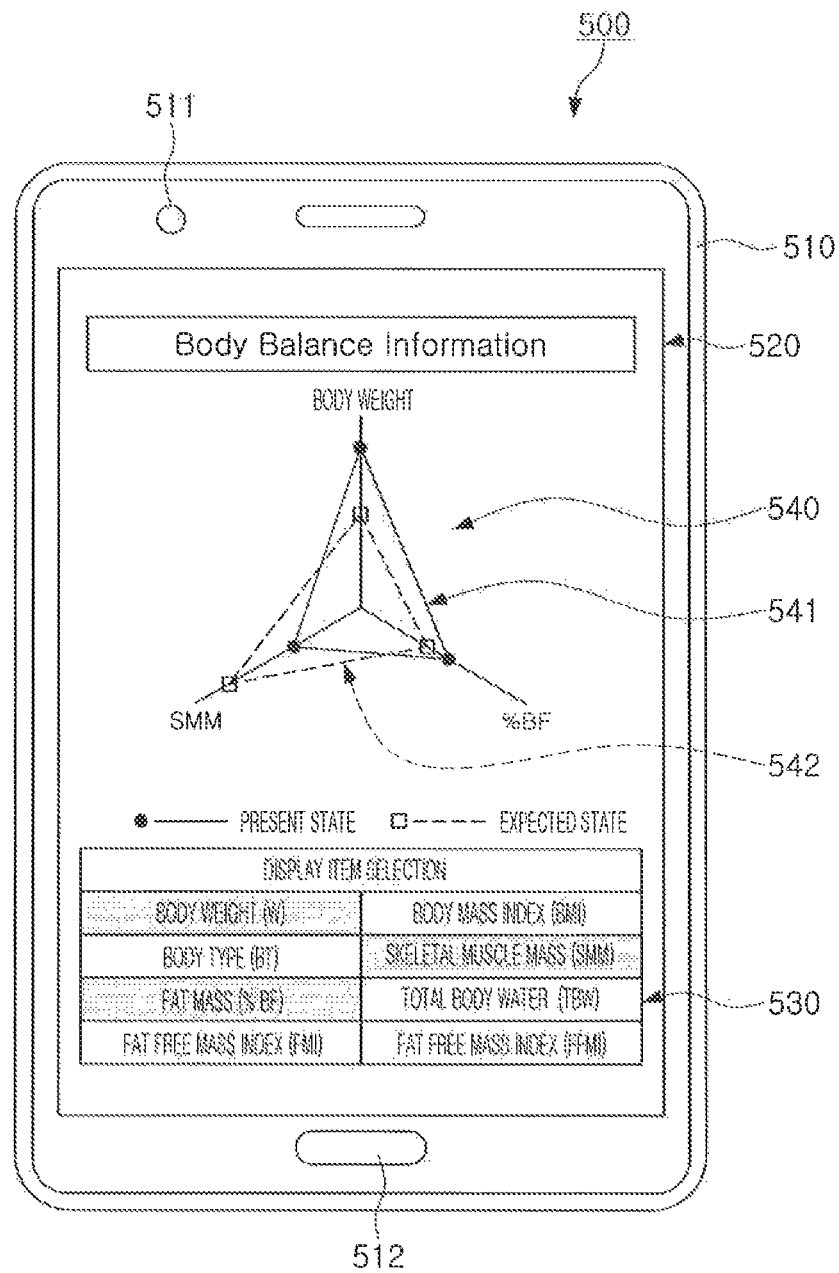
FIG. 16 is a view illustrating a method of providing a service according to an example embodiment of the inventive concept.
Figure 17:
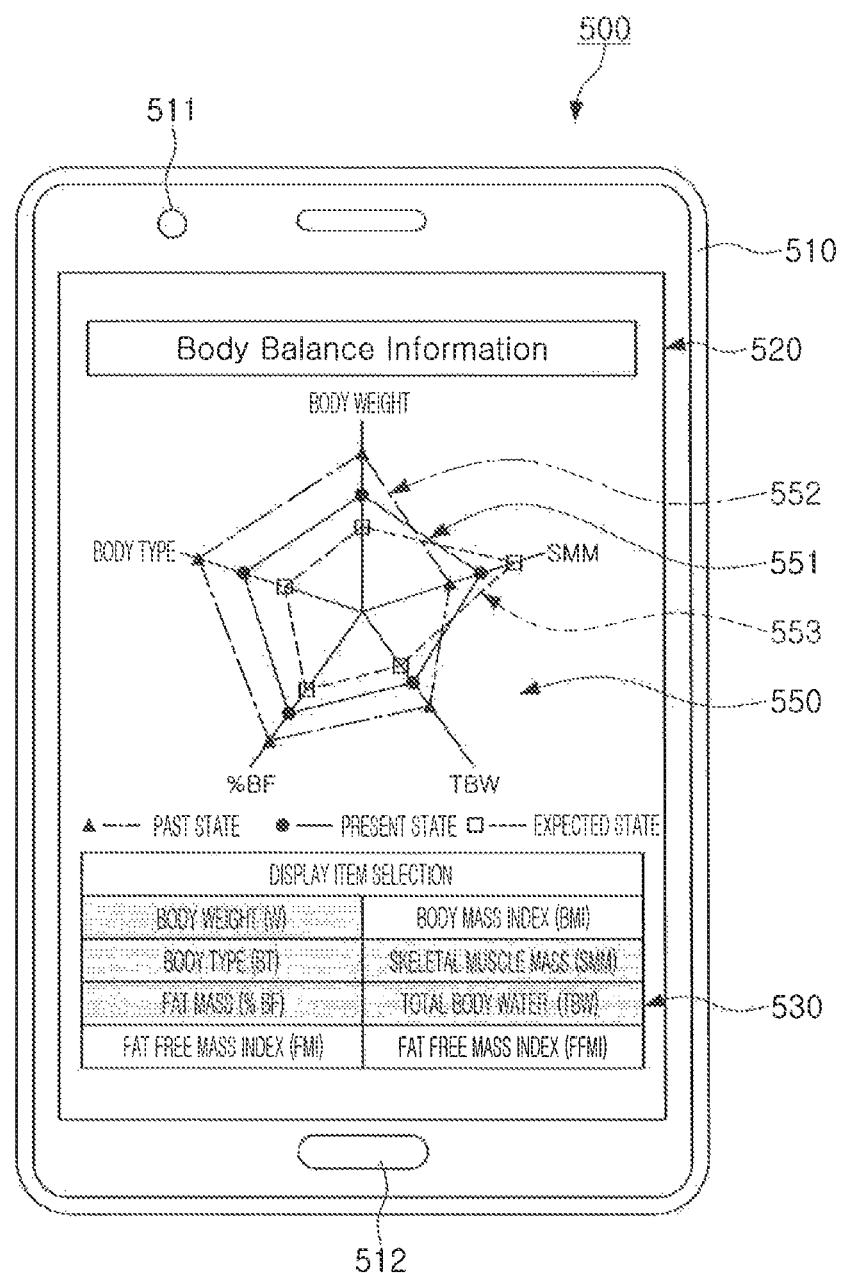
FIG. 17 shows a selection table and a resulting graph according to an embodiment of the inventive concept.
Figure 18:
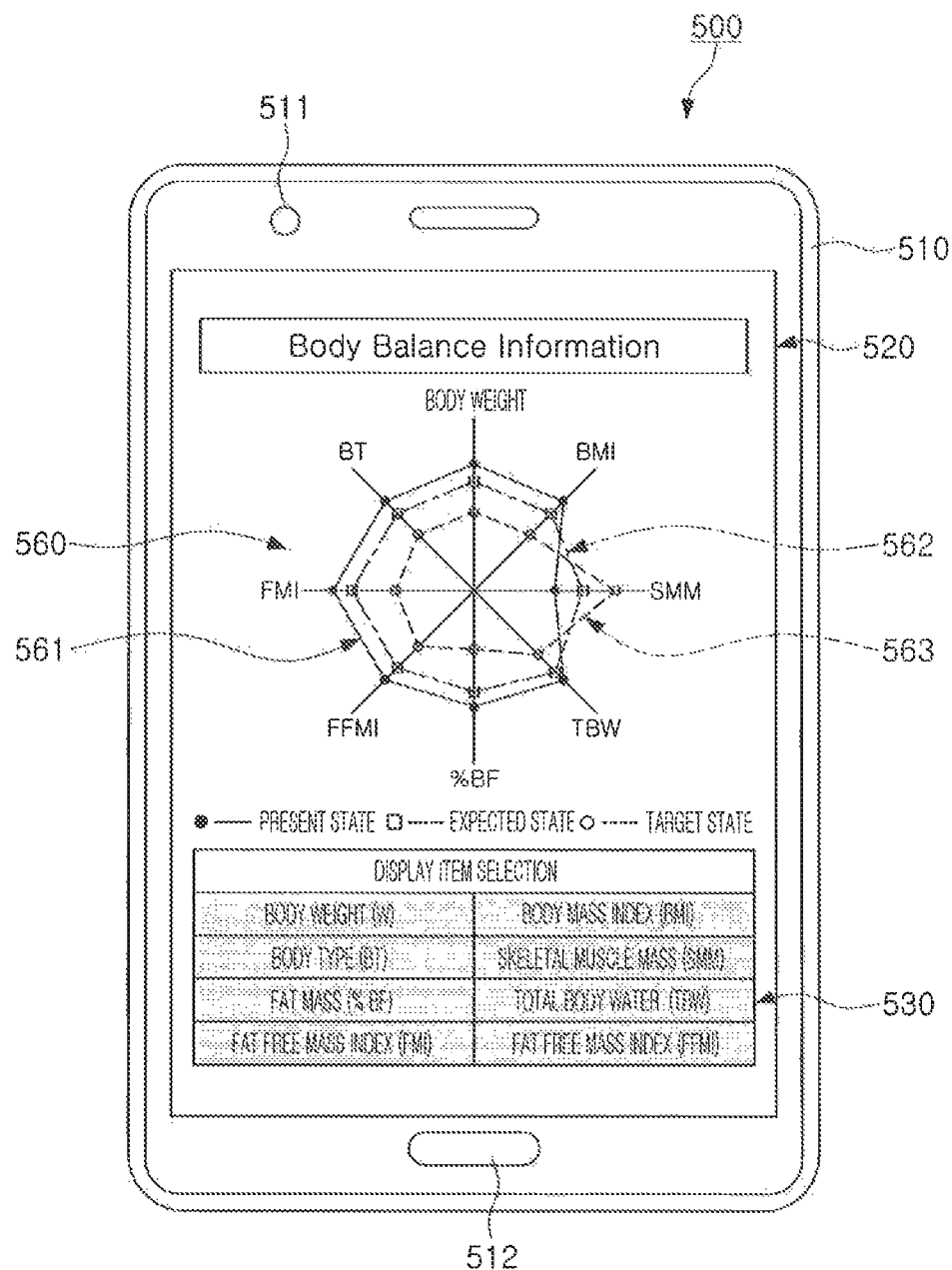
FIG. 18 shows a display of user-selected overall parameters displayed by a mobile device.

FIGS. 16, 17 and 18 are views illustrating a method of providing a service according to an example embodiment of the inventive concept.

FIG. 17 shows a selection table and a resulting graph according to an embodiment of the inventive concept, and FIG. 18 shows a display of user-selected overall parameters displayed by a mobile device.

FIGS. 16 to 18 illustrate a case in which the method of providing a service according to an example embodiment is provided through an electronic device 500. However, in a manner different from the case described above, the method of providing a service may also be provided using a wearable device, or the like, that a user wears on his body.

With reference to FIGS. 16 to 18, the electronic device 500 may include a housing 510, a camera 511, a fingerprint sensor 512, and the like. The camera 511 may be used to perform an authentication process, such as face recognition, as well as to capture an image. The fingerprint sensor 512 may perform an authentication process by detecting a fingerprint of the user. In an example embodiment, in a case in which the authentication process provided by the camera 511, the fingerprint sensor 512, or the like, is satisfactory, then a service according to an example embodiment may be provided. FIGS. 16 to 18 are merely examples of a service providing screen according to example embodiments, bat the inventive concept is not limited to shapes thereof illustrated in FIGS. 16 to 18.

With reference to FIG. 16, a display 520 may display a resulting graph 540, together with a selection table 530 in which a display item may be selected. In an example embodiment illustrated in FIG. 16, the user may have selected, weight, skeletal muscle mass, and fat mass in the selection table 530. In the resulting graph 540, parameters, such as body weight, skeletal muscle mass, and fat mass, selected by the user in the selection table 530 may be displayed.

The resulting graph 540 may include three axes corresponding to three parameters selected by the user. In an example embodiment illustrated in FIG. 16, the resulting graph 540 may display a first graph 541 displaying a present state of each parameter and a second graph 542 displaying a target state thereof input by the user, together. Through the resulting graph 540, the user may obtain information in which body weight and fat mass should be reduced, and skeletal muscle mass should be increased, to assist in reaching a goal. In an example embodiment, the electronic device 500 may further provide a service informing the user of a particular lifestyle that is recommended to reach a target, state set by the user in advance.

Subsequently, with reference to FIG. 17, on the display 520, the selection table 530 and a resulting graph 550 may be displayed. In an example embodiment illustrated in FIG. 17, the user may have selected body weight, body type, skeletal muscle mass, fat mass, and total body water, among parameters displayed in the selection table 530. The resulting graph 550 may include five axes corresponding to five parameters selected by the user.

In the meantime, in an example embodiment illustrated in FIG. 17, the resulting graph 550 may display a first graph 551 displaying a present state of each parameter, a second graph 552 displaying a past state thereof, and a third graph 553 displaying an expected future state thereof, together. In other words, the first graph 551 may be provided as a graph displaying a value of each parameter obtained at a first time point corresponding to the present time. The second graph 522 may be provided as a graph displaying a value of each parameter obtained at a second time point prior to the first time point, and such parameters may have been previously stored. In a case in which the present lifestyle, such as diet and an amount of exercise, is maintained, the user may determine an expected change in each parameter through the third graph 553 and control the diet, the amount, of exercise, or the like, based thereon.

FIG. 18 may illustrate an example embodiment in which the user selected overall parameters displayed in the selection table 530. A resulting graph 560 of FIG. 18 may include eight axes corresponding to eight parameters. In an example embodiment illustrated in FIG. 18, the resulting graph 560 may display a first graph 561 displaying a present state of each parameter, a second graph 562 displaying an expected future state thereof, and a third graph 553 displaying a target state thereof input by the user in advance, together. Thus, the user may determine lifestyle recommended to reach the target state by comparing the second graph 562 and the third graph 563. Alternatively, the electronic device 500 may inform the user of a lifestyle, such as types of exercise, the amount of exercise, diet, and sleep, that, are recommended to reach the target state by comparing the second graph 562 and the third graph 563.

Example embodiments described with reference to FIGS. 16 to 18 may be variously applied to each other. In an example embodiment, resulting graphs 540, 550, and 560 may display an entirety of a past, state, a present state, an expected, state, and a target state of parameters selected by the user in the selection table 530.

To summarize, in an example embodiment of the inventive concept, a plurality of parameters from among parameters included in body information, such as height, and body weight directly input by the user and biometric information obtained, by measuring bioelectrical impedance of the user may be displayed as a single resulting graph 540, 550, or 560. The user may determine the present state of his body more intuitively and easily in such a manner that the plurality of parameters among parameters included in the body information and the biometric information are displayed as a single resulting graph 540, 550, or 560.

As set forth above, according to example embodiments of the present inventive concept, a health management service, a body balance information service, and the like may be provided to a user using biometric information obtained by a biosensor. In addition to individually displaying different types of biometric information, useful information may be provided to a user by combining two or more pieces of biometric information, or a changing trend of biometric information may be provided to the user, thereby providing the user with a range of useful information using biometric information.

While example embodiments have been shown and described above, it will be apparent to those skilled in the art that modifications and variations could be made without departing from the scope of the present inventive concept as defined by the appended claims.

What is claimed is:

1. A method of providing a service, by an electronic device including at least one biosensor, the method comprising: measuring by the biosensor a bioelectrical impedance of a user at a first time point to obtain a first value representing a biometric information of the user;
   predicting, by a processor of the electronic device, biometric information of the user at a third time point subsequent to the first time point to obtain a third value, by utilizing the first value representing the biometric information of the user at the first time point and a second value representing biometric information of the user and measured by the biosensor at a second time point prior to the first time point, wherein the third time point is a future time point that has not yet occurred;
   calculating, by the processor, a difference between a fourth value and the third value, wherein the fourth value is a target value, representing target biometric information of the user, input by the user before the second time point; and
   outputting data to the user regarding a health management service and a diet management service based on the difference between the fourth value and the third value,
   wherein the electronic device provides a body type information by inputting a fifth value and a sixth value of the user, calculated from the bioelectrical impedance, to a database stored in the electronic device,
   the database includes information in which the body type information of the user is classified based on a trend line, the fifth value and the sixth value of the user, wherein the fifth value is provided as a Body Mass Index (BMI) and the sixth value is provided as a fat mass, and the trend line is defined on a 2-dimensional plane having a horizontal axis referring to BMI and a vertical axis referring to fat mass, and the body type information is determined based on a relative position of a point and the trend line, wherein the point has coordinates corresponding to the fifth value and the sixth value.

2. The method of providing a service of claim 1, wherein each of the first value, the second value, the third value, and the fourth value are provided as one among a fat mass, a muscle mass, a body mass index (BMI), a skeletal muscle mass, a fat mass index, a fat free mass index, and a total body water.

3. The method of providing a service of claim 1, wherein, in the measuring by the biosensor to obtain the first value representing the biometric information of the user at the first time point, the biometric information is measured based on body information input by the user, and the bioelectrical impedance.

4. The method of providing a service of claim 3, wherein the body information comprises at least one among a height, a body weight, a race, an age, and a gender of the user.

5. The method of providing a service of claim 1, wherein, in the outputting information to the user regarding the health management service, the user is informed of a change in a target body weight, based on the calculating of the difference between the third value and the fourth value, wherein the third value and the fourth value represent a fat mass of the user.

6. The method of providing a service of claim 1, wherein, in the outputting information to the user regarding the health management service, the user is informed of a change in a target body weight, based on the calculating of the difference between the third value and the fourth value, wherein the third value and the fourth value represent a muscle mass of the user.

7. The method of providing a service of claim 1, wherein, in the outputting information to the user regarding the health management service, the user is informed of a change in a target body weight, based on the calculating of the difference between the third value and the fourth value, wherein the third value and the fourth value represent a BMI of the user.

8. The method of providing a service of claim 1, wherein, in the outputting information to the user regarding the health management service, the user is informed of an amount of exercise, based on the calculating of the difference between the third value and the fourth value.

9. The method of providing a service of claim 1, wherein the first value, the second value, the third value, and the fourth value are linked to identity information of the user.

10. The method of providing a service of claim 1, wherein the fourth value is the target value for one of fat mass, skeletal muscle mass, or BMI, wherein the electronic device calculates a seventh value based on the fourth value, and wherein the seventh value is a target value of a parameter different from that of the fourth value.

* * * * *